United States Patent [19]

Vaillancourt

[11] Patent Number: 4,801,296

[45] Date of Patent: Jan. 31, 1989

[54] MEDICATOR SECURING DEVICE

[76] Inventor: Vincent L. Vaillancourt, 14 Bunyan Dr., Livingston, N.J. 07039

[21] Appl. No.: 80,991

[22] Filed: Sep. 11, 1987

Related U.S. Application Data

[62] Division of Ser. No. 628,641, Jul. 6, 1984, Pat. No. 4,704,177.

[51] Int. Cl.$^4$ ............................................. A61M 5/00
[52] U.S. Cl. .................................. 604/272; 604/905; 285/915
[58] Field of Search ............... 604/180, 93, 110, 111, 604/174, 179, 189, 200, 246, 283, 321, 344, 905, 272; 128/DIG. 26, 293; 285/915, 293

[56] References Cited

U.S. PATENT DOCUMENTS

| | | | |
|---|---|---|---|
| 986,655 | 3/1911 | Taylor | 604/307 |
| 3,574,306 | 4/1971 | Alden | 604/174 |
| 3,782,377 | 1/1974 | Ryhcik | 128/DIG. 26 X |
| 3,973,565 | 8/1976 | Steer | 604/180 |
| 4,059,105 | 11/1977 | Cutruzzula et al. | 604/180 X |
| 4,149,534 | 4/1979 | Tenczar | 604/905 X |
| 4,221,215 | 9/1980 | Mandelbaum | 128/DIG. 26 X |
| 4,324,237 | 4/1982 | Buttaravoli | 604/180 |
| 4,485,809 | 12/1984 | Dellas | 604/307 X |
| 4,534,762 | 8/1985 | Heyer | 128/DIG. 26 X |
| 4,669,458 | 6/1987 | Abraham et al. | 128/DIG. 26 X |

FOREIGN PATENT DOCUMENTS 0051935  5/1982  European Pat. Off. ........ 128/132 D Primary Examiner—Stephen C. Pellegrino
Attorney, Agent, or Firm—Kenyon & Kenyon

[57] ABSTRACT

This invention pertains to a medicator securing device for use in an I.V. administration in which a needle is inserted into a resilient cap member to add drugs and the like to an infusion procedure. This inserted needle is retained in inserted condition and position in this cap by this securing device. A flexible, substantially transparent plastic film having one surface coated with a self-stick adhesive is applied tightly to a frame of semi-rigid material. This frame provides at least one window-like opening which is covered by the adhesively-coated film. A release sheet member is applied to the window-like area until a time of use and application of the securing device, at which time the release sheet is removed and the adhesive surface of the film within said window is brought to and around the connection, with a fold made of the device so that the film is engaged tightly around the connection. At the time of removal, said frame portions are grasped to pull the adhesive surfaces of the film within the window-like area apart for removal or exposing of the connection. This device is also depicted as securing a Luer slip connection and being made with the frame and the window-like area protection of a same release-sheet material.

15 Claims, 4 Drawing Sheets

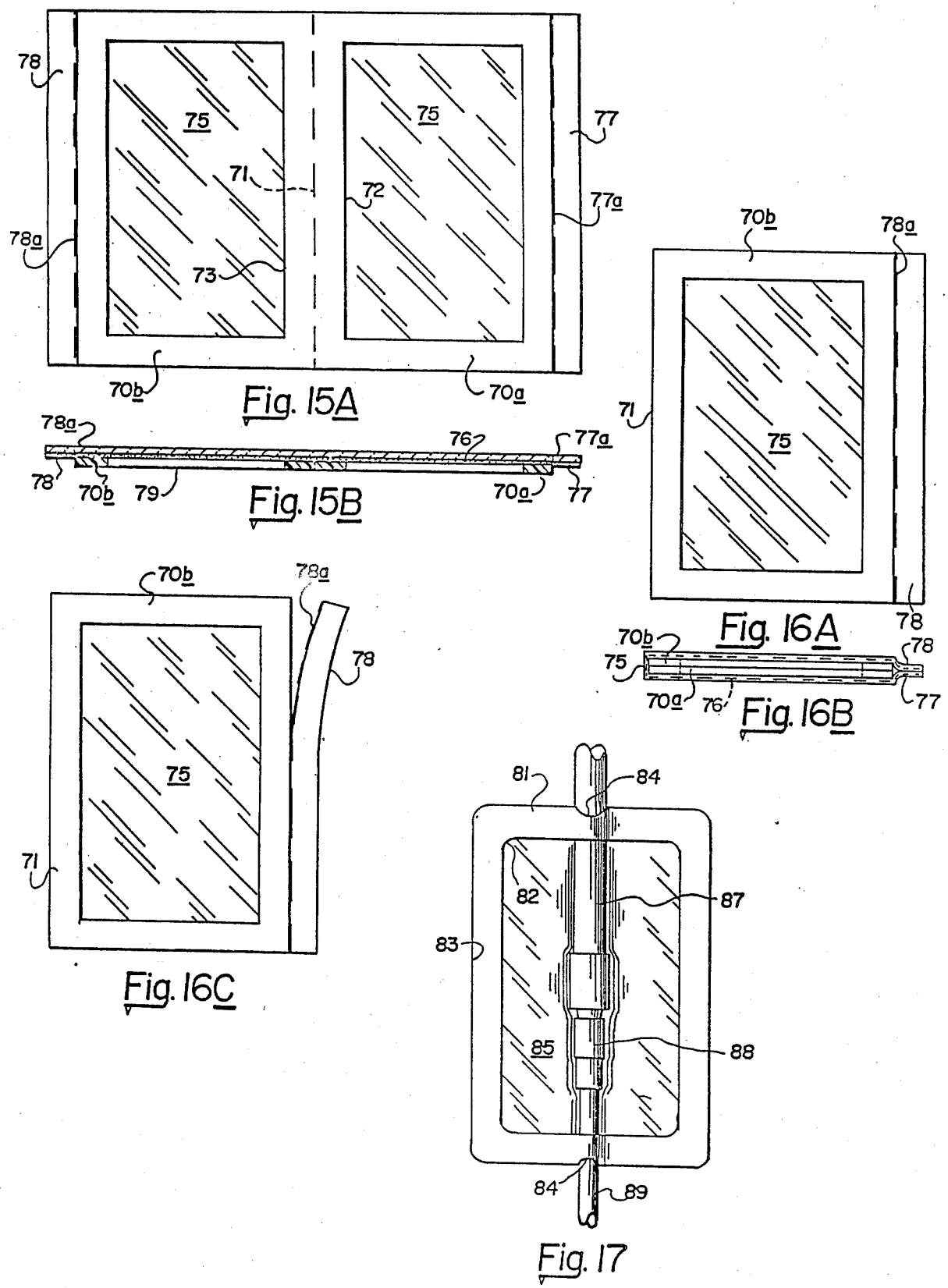

MEDICATOR SECURING DEVICE

CROSS-REFERENCE TO PRIOR APPLICATION

This application is a divisional of my U.S. application Ser. No. 628,641 as filed July 6, 1984 now U.S. Pat.No. 4,704,177.

BACKGROUND OF THE INVENTION

1. Field of the Invention

This invention relates to a medicator securing device. This securing device employs adhesively-coated clear and flexible plastic so that observation of flow and/or addition of medication can be observed by the attendant.

2. Description of the Prior Art

The use of an adhesive coating on plastics, particularly thin and flexible plastic film, is very well known. Adhesive tape is and has been used with catheters and the securing of these members to the body parts of the patient being treated. Of note is U.S. Pat. No. 4,485,809 which provides a thin film dressing for a wound of the skin of a patient. Also of note is U.S. Pat. No. 986,655, as well as U.S. Pat. No. 3,046,984 wherein a retaining member is suggested to be of aluminum foil with an adhesive surface. Retention of a secondary conductor and needle is with a slot, and viewing of the flow in the flexible tubing is through a rectangular opening. The simplified but novel securing device of this application is not shown or suggested. Also of note is U.S. Pat. No. 3,430,300 which shows a strip of flexible material with an adhesive surface and a release paper used therewith. The retention of a tube is with a loop formed around the tube and with extending wings of an aperture and wing members inserted through the aperture to secure the tube. Also noted is U.S. Pat. No. 3,918,446 which This patent depicts a fold-over device with appropriate cutouts for guiding the hookup connection and the tubing and to effect a retained and positioned placement. As additional adhesive is provided for securing the device to the skin of the patient. This device is for retaining the I.V. hookup to and into the vein or artery of a patient. This device does not show or suggest a thin, transparent plastic sheet with peripheral frames to permit ready removal from the added inserting site. U.S. Pat. No. 4,120,304 shows an adhesive member of flexible material and an added clamp member of molded material.

It is to be noted that, frequently, supplementary medications and/or fluids are fed into I.V. lines using secondary administration sets. This invention is directed to and toward such situations and conditions. In these cases, the normal means of hookup is to attach a needle at the end of a luer connector of the secondary set and insert (inject) a needle into a rubber cap at a "Y" site conventionally provided at and on the primary I.V. line. Although there is some frictional resistance to withdrawal of the needle from the rubber cap resulting from the inherent elasticity of the rubber, this resistance is insufficient to assure the practitioner (nurse, physician, etc.) that accidental withdrawal does not occur. Hence, it is standard practice and policy in most hospitals after making such a hookup to tape the two components (needle and rubber cap) together. This procedure is cumbersome, time-consuming and, unless done properly, may represent a contamination site. (During taping, it is relatively easy to move the needle backward and forward in the rubber cap, thus preventing a site that is contamination-suspect.) This procedure also requires much dexterity. When breaking the connection, there is no simplified procedure (some nurses cut the tapes with a scissor, others unwrap the tape). In any case, as no consideration by the attendant was given to removing the tape at the time it was applied, it is not a standard or routine procedure and, hence, presents a potential site for contamination due to above-identified conventional procedure. Partly as a result of this, more often than not the connection, once made, is not broken. This is not always possible for, unfortunately, there are many cases where this connection must be broken—for example, when feeding drugs—and the hookup site must be opened to replace the secondary needle with another needle to add a second or third drug.

SUMMARY OF THE INVENTION

This invention may be summarized, at least in part, with reference to its objects. It is an object of this invention to provide, and it does provide, a securement device utilizing a thin, transparent plastic sheet (film) coated on one side with an adhesive and having a border frame at least along three sides, with said frame portions on their exposed surfaces absent adhesive and available to be grasped so as to provide ready separation of the adhesive surfaces of the facing films when brought together. The film sheet is sufficiently flexible to engage and hold the injection needle in position within the rubber cap at a "Y" site connector. This securement device may also be used in retaining a connection of male and female Luer lock connectors.

A further object of this invention is to provide, and it does provide, a securement device that is adaptable to automatic production and to be removed from a protective sheath or with a tearaway portion to provide storeable assembly until prepared for use.

This invention, to be described more fully, is directed to a satisfactory overcoming of the above-mentioned concerns and difficulties. This securement device provides an easy-to-use means for securing a needle and connection tubing carrying medication, such as drugs, into a "Y" site. This same securing device is depicted with Luer lock connectors used therewith. This securing device retains the needle so that it is virtually impossible to pull the needle out of the rubber cap. More importantly, it provides a standard procedure for readily removing the securement device without risk of site contamination. This securement device includes a thin film that is clear so that, after attachment, the practitioner is able to readily inspect the site to determine the location and retention of the secondary needle within the rubber cap and whether or not there is any leakage which sometimes occurs.

This securement device includes a thin layer of plastic deformable film, preferably polypropylene, to which an adhesive layer has been applied. In one embodiment, the film is framed on the adhesive side with a strip of paper, plastic film or other material which gives some bulk to the adhesive film and allows it to retain its shape when held, say, at one corner. Yet the framing material is not so rigid that it cannot be readily deformed when subject to finger pressure. On one set of opposite sides, the framing material may be scored for ease of bending. In the supplied condition, the entire face of the adhesive surface of the plastic film within the frame is protected with a release sheet. At the time of use, the release sheet is removed, exposing the adhesive film and non-tacky (no adhesive) frame. The framed adhesive strip is placed in back of the connectors (coupled), properly positioned, and then folded (in pocketbook fashion) around the connector members. The adhesive film is pressed against the connector members to contour the adhesive tape to the connector site and rubber cap, thereby providing a tight bond and assuring significant pullout strength so that the connector members may not be pulled apart or moved accidentally. In this manner, the adhesive film forms "a second skin" around the connector members, taking on the shape of the connector and cap and associated members. When the time comes that the connection is to be broken, the medicator securing device may be removed readily by grasping it at the frame and pulling apart. The adhesive film readily disengages from the connector members in a simple, one-step, disengaging procedure.

The frame permits ready separation and removal of the securement device as and when desired. This removal does not alter the original placement of the secured components and may be reused as hookup retention in the desired use.

These and other objects and advantages of the invention will become more apparent from the following detailed description taken in conjunction with the accompanying drawings wherein:

BRIEF DESCRIPTION OF THE DRAWINGS

FIGS. 15 A and 15 B represent plan and end views of the medicator securing device of FIG. 5, but with the film and adhesive surface portion extending beyond the sides thereof to provide edge retention means;

FIGS. 16 A, 16 B and 16 C represent plan, end and a face view with an edge retain portion partly severed by a tearing actuation. FIG. 16 A represents the securing device of FIG. 15 A in a folded condition ready for shipment and with the extending edge portions of the film pressed together. FIG. 16 B represents the device of FIG. 16 A prior to tearing away the retaining edge portions, and FIG. 16 C shows this protruding edge portion being removed with a tear actuation;

FIG. 17 represents a plan view of yet another alternate construction of a securing device, the secured connection depicting a Luer lock with male and female end member portions in fluid-conducting and secured position;

FIG. 18 A shows a plan view of yet another alternate construction of a securing device. FIG. 18 B represents a sectional view taken on the line 18 B—18 B of FIG. 18 A and looking in the direction of the arrows, this view partly diagrammatic as to the thickness of the components to illustrate their relationship to each other. FIG. 18 C represents a plan view of the device of FIG. 18 A with the release-sheet portion depicted in a partly removed condition, and FIG. 18 D represents the device of FIG. 18 C with the release sheet removed and folded so as to retain this connection;

FIG. 19 B represents a fragmentary sectional view in a greatly enlarged and exaggerated scale to illustrate the construction of said securing device, this view taken on the line 19 B—19 B of FIG. 19 A and looking in the direction of the arrows.

EMBODIMENT OF FIGS. 1 THROUGH 4

Figure 2:
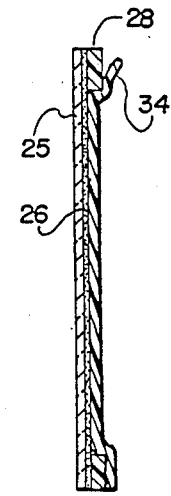
FIG. 2 represents a sectional view taken on the line 2—2 of FIG. 1 and looking in the direction of the arrows, the thickness of the several components exaggerated for the purpose of illustration and relationship of these components to each other.
Figure 1:
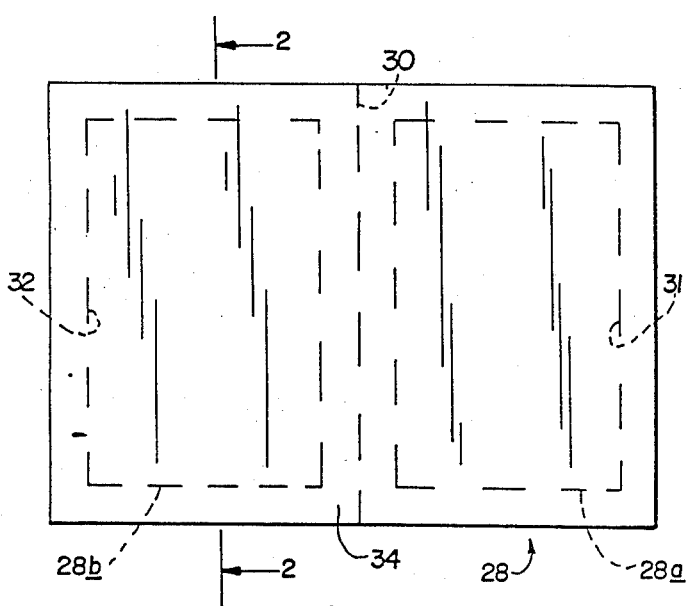
FIG. 1 represents a face or plan view of a medicator securing device in which the frame is rectangular.

Referring next to the drawings, and in particular to FIGS. 1 through 4, there is shown a configuration in which the frame of the device is of a rectangular shape having four edge portions. In FIG. 1, the security device is shown in an assembled and laid-out condition with a release-sheet member positioned and placed over the frames and film extents within the frame. A sectional view of the device is shown in FIG. 2 to illustrate the relationship of the elements to each other.

In FIGS. 1 and 2, this device is depicted as having a thin film sheet 25 with substantially transparent properties and flexibility to accommodate bending and forming without rupture. Among the contemplated films that may be used are: polyethylene, polypropylene, polyethylene terephthalate, polyurethane, polyvinyl chloride (PVC), or combinations thereof. There are also many other plastic films that may be used, but cost is a consideration. The thickness of this film is usually about one-half to four-thousandths of an inch, but the thickness is determined by the strength and properties of the selected plastic. Said film 25 is coated on one side with an adhesive 26 with flexible and self-adhering properties. Such films and adhesive coating are quite conventional. To this adhesive surface is positioned and retained a thin frame 28 which may be from one sheet of material die-cut to shape or may be of two pieces arrayed in side-by-side construction. At the mid- or fold-line 30, this frame is scored when the frame is of one-piece construction or when two pieces are positioned to be in side-by-side close proximity. In both the right-and-left frame portions 28 a and 28 b, there are formed substantially like cutouts 31 and 32. The views of FIGS. 1 and 2 anticipate the presence of a release sheet 34 to protect the exposed surface of the adhesive 26.

As seen in FIG. 2, the security device of FIG. 1 is shown in section, with the thicknesses of the assembled material exaggerated for the purpose of illustration. As reduced to practice, the film 25 is usually from one-half to four-thousandths of an inch in thickness. This film within the frame is absent of any perforation and has sufficient strength so as to retain the placed conductor and connector without stretching which could cause movement of the conductor relative to the connector. Adhesive coating 26 is a commercial product and is usually about one-half to four-thousandths of an inch in thickness, but this is a matter of selection with consideration of the composition of film 25 and a compatible adhesive for use therewith. The material for the frame may be of surgical grade kraft paper of forty- to one-hundred pound stock, may be release paper stock, or may be of plastic of a few thousandths of an inch in thickness. The material for the frame 28 is made so that said frame will adhere to the adhesive coating 26 with the opposite and outwardly-facing surfaces of the frame 28 absent a surface or treatment, tending to make siad surfaces attract each other. The release-sheet member 34 is usually of a wax-treated, paper-like material or may be of a plastic that does not stick to the adhesive surface 26. Release-sheet materials having such properties are well known.

PLACING OF NEEDLE AS IN FIGS. 3 AND 4

Figure 3:
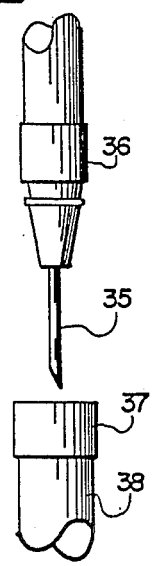
FIG. 3 represents a connector and attached needle in proximity for insertion of a needle into a resilient cap of a "Y" connector.
Figure 4:
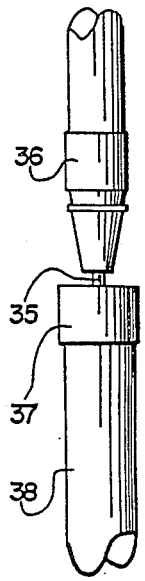
FIG. 4 represents a diagrammatic and partly fragmentary view showing said needle of FIG. 3 inserted into the resilient cap of the connector.

In FIGS. 3 and 4 is depicted the positioning and placement of a needle 35, which is conventionally a part of a connector generally identified as 36. FIG. 3 shows the needle 35 ready for insertion into a rubber cap 37 of a tubing connector member 38. In FIG. 4, needle 35 is shown as inserted into said rubber cap 37. This connector member 38, or intermittent injection cap, is conventionally an inserting-site means provided in a "Y" -site device provided as a portion or section in an I.V. length of tubing. As depicted, the needle 35 is shown inserted in FIG. 4 and the initial puncture of the resilient cap 37 is under asceptic conditions. The continued use in the patient lends itself to sliding of the needle in the now-punctured cap, and this sliding or in-and-out movement of the needle 35 in the cap 37 leads to potential contamination which the security device of this invention prevents.

SECURITY DEVICE AS IN FIGS. 5, 6, 7 AND 8

Figures 6, 7:
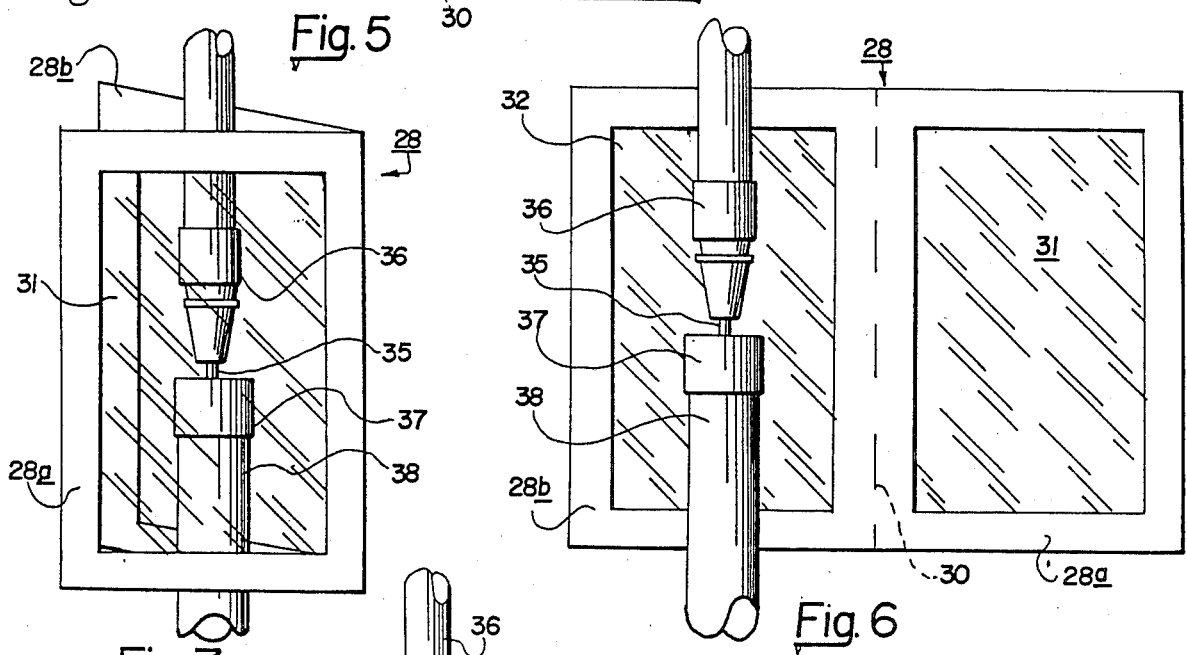
FIG. 6 represents the plan view of the medicator securing device of FIG. 5 with the needle and connector cap of FIG. 4 now positioned for application of the securing device.
FIG. 7 represents a view of rotation into position of one-half of the securing device.

In FIGS. 5, 6, 7 and 8, the security device is shown as used and employed for retention of placed needle 35 into cap 37. The initial insertion and positioning are done with careful attention by the attendant who then removes the release-sheet member 34 (as in FIG. 5) and exposes the adhesive coating 26 within the frames 28 a and 28 b. The connection (as in FIG. 4) is now placed in position on portion 28 b (as shown in FIG. 6) and with adhesive-coated surface 26 engaging and partially retaining the connected members. In FIG. 7, the right-hand portion of the security device is in the process of being folded over the connectioin and the adhesive surfaces are brought together using the fold line 30 to effect bringing the frame portions 28 a and 28 b into more or less a coincident arrangement. The attendant then presses the adhesive surfaces together and the frame portions 28 a and 28 b are manipulated to tightly engage the tubing connector portions 36 and 28.

USE AND OPERATION OF THE SECURITY DEVICE

It is contemplated that this security device with release-sheet member 34 in place be shipped to the use site in a protective box, wrapper or envelope. This security device may or may not be in a sterile condition depending on the securing requirement for the connecting members and the device. The pathway in the connected pathway, however, is in sterile condition prior to use of the securing device. With the fluid flow path completed, the release-sheet member is removed from the adhesive surfaces after the connection of FIG. 4 has been made. The thin, flexible film portions 25 are brought to and around the connector components to tightly retain these components in the desire position. The plastic film and the adhesive surface thereon provide a tight seal and retention of the components.

Figure 8:
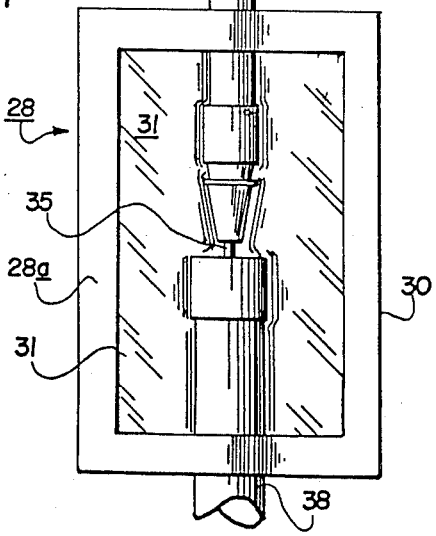
FIG. 8 represents the securing device of FIG. 7 showing in plan view the securing device in fully applied position.

It is contemplated that the device will remain in the mounted and retaining position of FIG. 8 while the needle 35 is inserted in the cap 37. It is to be further noted that the outer surfaces of this device have no adhesive surface allowing placement of the needle and manipulative movement of this retained needle for the desired period of time. If there is need of withdrawing needle 35 from the cap 37 for the insertion of another needle or a substitute needle with another medication, the frame portions 28 a and 28 b are utilized.

EMBODIMENT OF FIG. 9

Figure 9:
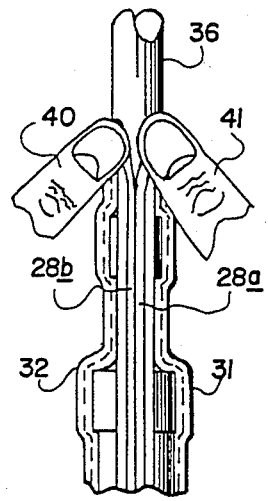
FIG. 9 represents a side view of the securing device of FIG. 8 with finger means for producing a separation of the device.
Figure 18A:
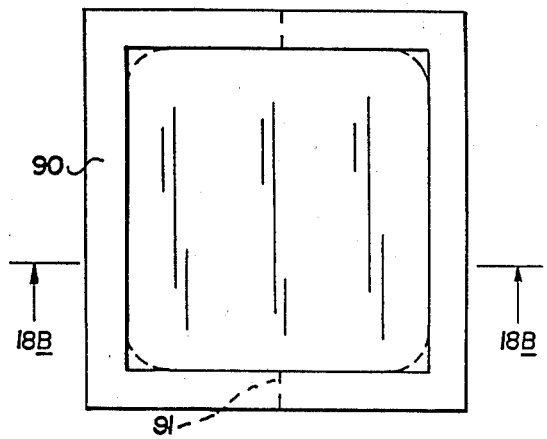
FIGS. 18 A, 18 B, 18 C and 18 D represent plan, end and face views with a release sheet partly removed and the device in applied securing position.
Figure 18D:
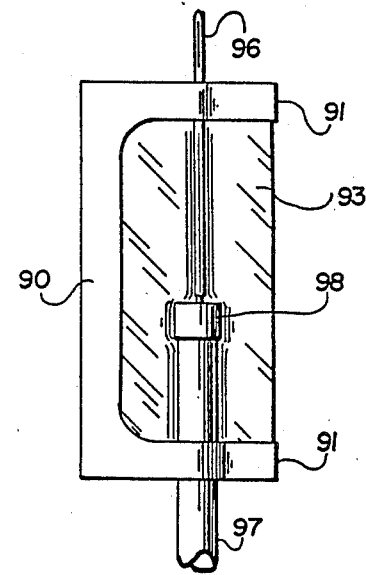
Figure 18B:
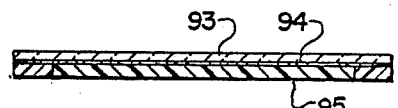

FIG. 9 illustrates the means and method of separation and removal of the securing device from a connection site. As depicted, the frame portions 28 a and 28 b are grasped by fingers 40 and 41 which manipulate these frame portions to effect the desired separation. Said frame portions at their contiguous faces do not bond to each other, but are readily separable. These portions are caused to be moved apart and further and continued separation by pulling apart is made so that the adhesive surfaces on the portions 30 and 31 are brought to a more-or-less flat condition. Where a needle insertion is made as in FIG. 8, the needle 35, connector 36, cap 37 and connector 38 are exposed and may be removed or separated. If and when needle 35 and connector 36 are to be replaced with another needle and connector, and security device may be reused since the adhesively-coated flexible, thin film may still be usable whereby the operations of FIGS. 6, 7 and 8 are repeated.

ALTERNATE SECURING DEVICE AS IN FIGS. 10, 11 AND 12

Figure 10:
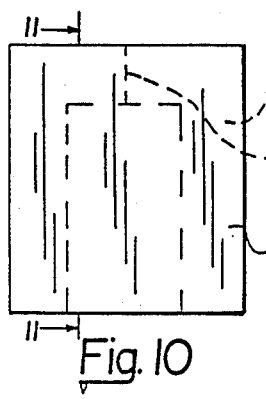
FIG. 10 represents a plan or face view of an alternate construction of a securing device in which the frame portion is of "U" shape.
Figure 11:
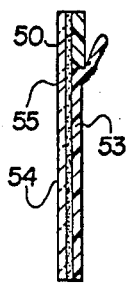
FIG. 11 represents a side sectional view taken on the line 11—11 of FIG. 10 and looking in the direction of the arrows, the thickness of the several components exaggerated for the purpose of illustration and relationship to each other.
Figure 12:
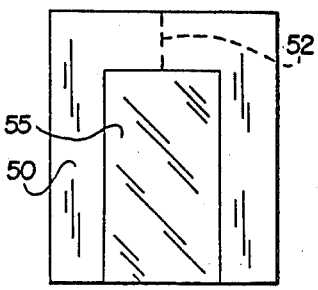
FIG. 12 represents the plan or face view of the securing device of FIG. 10, but with the release sheet removed from the adhesive surfaces of the flexible film.

In FIGS. 10, 11 and 12, there is shown an alternate construction of and for a securing device. Rather than the rectangular frame of FIGS. 1 and 5, an alternate frame may be provided in which the frame is "U"-shaped with a frame identified as 50, which is preferably made with a score 52 providing a fold line for this device. A thin, flexible, substantially transparent film 54 having an adhesive surface 55 applied thereto has the exposed adhesive surface protected from unwanted attraction to another surface by a release sheet member 56. In FIG. 10, said alternate construction shows the frame 50 with a release-sheet member 56 disposed toward the near side. FIG. 11 shows a side view of the security device of FIG. 10 with the release sheet 56 ready for removal. The FIG. 12 shows the device ready for use with the release sheet 56 removed and the adhesive surface 55 exposed.

USE OF THE ALTERNATE EMBODIMENT OF FIGS. 13 AND 14

Figures 13, 14:
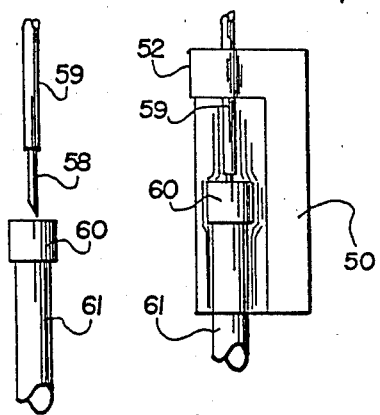
FIG. 13 represents a more-or-less diagrammatic view of a needle and resilient cap and connector very similar to that depicted in FIG. 3.
FIG. 14 represents the alternate security device of FIG. 12 folded into the securing condition for the assembled connector of FIG. 13, a needle member being inserted into a resilient cap portion of a connector and the security device having the resilient film portion and the adhesive surface portion thereof tightly pressed in and around the connector members.

In FIG. 13, a needle 58 connected to a flexible conductor 59 is depicted as ready for insertion into a resilient cap 60 which is provided on a connector 61. In FIG. 14, the needle 58 is shown inserted into cap 60 in the manner of FIG. 4 above. This connection is retained by the security device of FIG. 12 which is folded at score 52, and the flexible film 54 is caused to be brought tightly around the connector portions. The frame 50 is adapted to be manipulated (as in FIG. 9) to pull the flexible films apart.

The "U"-shaped frame 50, as in frame 28 in FIGS. 6 and 7, is folded at score 52 and the flexible film 54 is caused to be brought together with the adhesive surface 55, tightly engaging the connector portions 59, 60 and 61. When it is desired to remove the security device of FIGS. 10, 11 and 12, the frame leg portions or extending legs are grasped by the attendant and at the frame legs the pulling apart exposes the connector and resilient cap. The needle may be withdrawn for the insertion of another needle and connector for another drug or for the discarding as in the prior disclosed embodiment for frames of four sides. It is to be noted that the needle 58 and conductor 59 are smaller than in FIGS. 3 and 4. In like manner, the cap 60 and connector 61 are likewise smaller in diameter. This reduced size is to indicate that said securing device is applicable to the many sizes and configurations provided by the manufacturers of I.V. components and the several uses including for infants.

EMBODIMENT OF FIGS. 15 A AND 15 B

Figure 5:
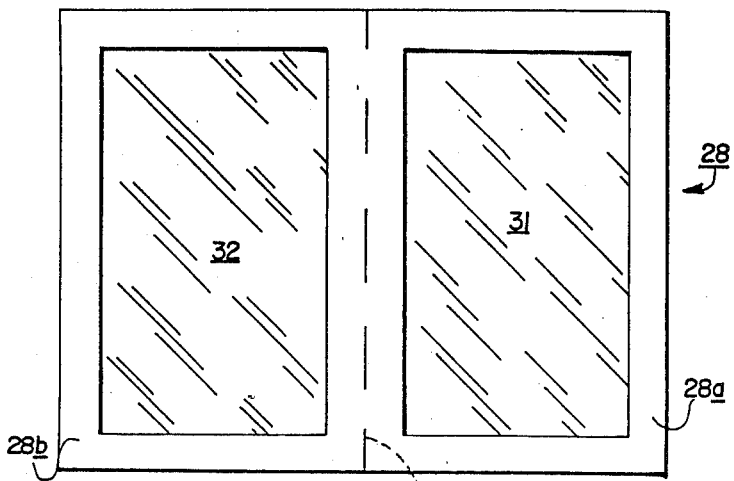
FIG. 5 represents the plan view of the medicator securing device of FIG. 1 with a release-sheet member removed.

In FIGS. 15 A and B, the securing device of FIG. 5 is depicted but rather than the film stopping at the edges of the frame, the film and adhesive coating thereon are extended along two edges to provide a retention means of the device until ready for use. In these FIGS., a frame 70 a and 70 b includes a serration or score 71 at the midpoint to enable folding at a predetermined point. Said frame provide and include right and left window portions 72 and 73. A film 75 having an adhesive coating 76 thereon is like the films above discussed. This embodiment contemplates a film 75 having an adhesive coating 76 facing toward frame 70 a and 70 b. This film and adhesive coating are made wider than the frame 70 a and 70 b so that extending portions 77 and 78 have the upper surface with adhesive ready for manipulative folding and closing for storage. A release sheet 79 is made of a width to cover the exposed surface of the window portions 72 and 73. Said release sheet may be sized to be placed adjacent one window portion whereat this release sheet is conditioned with both surfaces easily removed from the adhesive surfaces.

EMBODIMENTS OF FIGS. 16 A, 16 B AND 16 C

In FIGS. 16 A, 16 B and 16 C, the security device of FIGS. 15 A and 15 B is shown in the folded condition for shipment to the intended use site. In FIG. 16 C, the device is at the initial stage for use. In FIGS. 16 A and 16 B, the securing device is viewed in a folded condition with the extending portions 77 and 78 in a contiguous position and condition. Frame portions 70 a and 70 b are also in contiguous relationship and release sheet 79 is therebetween. If the release sheet is of a width to cover window portions 72 and 73, the release sheet is in a folded condition. If the release sheet is conditioned on both surfaces, then the release sheet 79 need be only wide enough to cover one window. This is a matter of a selected production process. The release sheet is adapted for easy removal after the extending portions 77 and 78 have been removed. Where and when sterilization is desired or required, this is done by conventional methods. The connection of the I.V. components provides a conducting path with desired sterility before application of the securing device.

In FIG. 16 C there is depicted the securing device of FIG. 16 A and showing the extending edge portions 77 and 78 being partially removed. Perforations 77 a and 78 a are provided for ease of removal of said extending edge portions so that the device may be applied for use as in FIGS. 6, 7 and 8 above described.

EMBODIMENT OF FIG. 17

In FIG. 17 an alternate frame is depicted as retaining a Luer connection. Frame 81 is shown with external and with internal rounded corners 82, but may be made with sharp corners if and when desired. This securing device is folded preferably along long edge 83 and with or without extending edge portions removed as by tearing shown in FIG. 16 C. The frame 81 may have tab cutouts 84 to provide manipulating access portions for locally engaging a release sheet positioned between the self-stick adhesive surfaces of a film identified as 85. As shown, this connection is with male and female Luer slip connection ends, with tubing conductor 86 terminating with a connector half 87 which is mated with a compatible connector 88 attached and forming a terminal end of a tubing, conductor 89. Connections other than for Luer slip configurations are contemplated since this retaining device is for a made connection in a desired attitude and condition.

EMBODIMENT OF FIGS. 18 A, 18 B, 18 C AND 18 D

Referring next to yet another concept of a securing device, as in FIGS. 18 A, 18 B, 18 C and 18 D, there is depicted a frame 90 which may be square or rectangular. This frame 90 is scored at 91 to provide a desired fold line of the frame. Although the outer corners are substantially square, the inner corners of the frame are depicted with an arcuate configuration 92. A flexible film 93 is like that described in other prior embodiments. This film 93 is coated with adhesive 94 and said film and adhesive coating extend to the outer extents of the frame 90. The frame is placed on the adhesive surface and pressed thereto so as to secure this frame to the film. A release-sheet portion 95 is cut to fit inside the frame sides, but the corners of this release sheet are left in a square condition to extend and lie over the arcuate corners 92 so that the overlaid corner portions of the release sheet provide means for sliding the fingernail of the operator under said corner or corners to provide grasping means for the removal of the release sheet from the adhesive surface 94. The release sheet may also be made larger so as to extend intermediate the inner and outer edges of the frame 90, but this is a matter of selection and cost as high-speed assembly is contemplated.

In FIG. 18 B, the securing device of FIG. 18 A is depicted in section, but the thicknesses of the several members are diagrammatically shown for illustration. The flexible film is usually one-half to four-thousandths of an inch in thickness, and in like manner the frame 90 is only a few thousandths of an inch in thickness and the self-stick adhesive applied thereto is usually one-half to about four-thousandths of an inch in thickness. The release sheet may be two- to ten-thousandths of an inch in thickness when of paper or may be less than one-thousandth of an inch when of plastic.

FIG. 18 D represents a plan view of the securing device with the release sheet 95 removed, the frame 90 folded at score 91, and with the film 93 tightly pressed around conductors 96 and 97 to retain a needle (not identified) in resilient cap 98. This use of the securing device of this embodiment is as described in connection with prior embodiments.

EMBODIMENT OF FIGS. 19 A AND 19 B

Figure 19B:
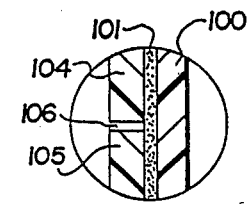
FIG. 19 A represents a plan view of an alternate securing device in which the frame and center release-sheet portion is from the same release-sheet material.
Figure 18C:
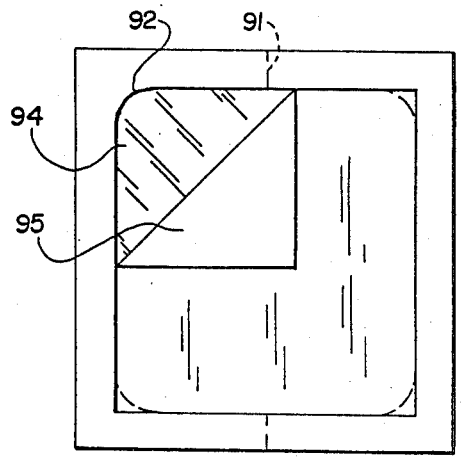
Figure 19A:
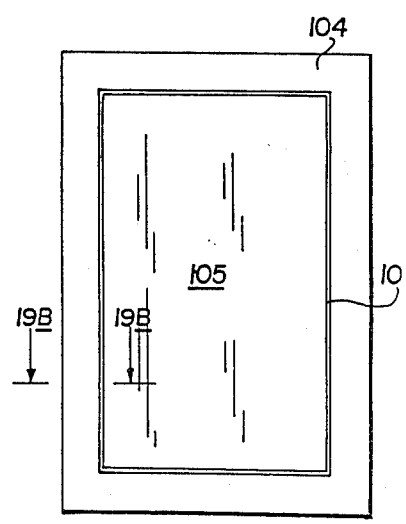

In the embodiment of FIGS. 19 A and 19 B, there is depicted a connection securing device which, as shown, is very similar to that of FIG. 18 A, but rather than a frame of dissimilar material to that of the release sheet this embodiment utilizes only a flexible film with a self-stick adhesive on one face or surface. A release sheet of semi-rigid properties provides the frame and the interior protective, removable release-sheet member for the window-like opening. It is to be noted that although shown as a rectangular member, the frame may be made in a U-shape similar to that shown in FIG. 12.

As depicted in FIGS. 19 A and 19 B, a flexible film 100 is similar to those flexible films described in connection with above-and prior-discussed devices. A self-stick adhesive 101 is applied to this film and is quite conventional. A frame 104 has a release-sheet interior member 105 cut to fit adjacent the interior edges of the frame 104. In high-speed production, die means is used to produce a cut 106 made in the release-sheet material. This release-sheet material is die-cut to also provide the exterior and inner edges of frame 104 and cut 106. Both the frame 104 and member 105 are applied and pressed to the self-stick surface 101 of the film 100. The release-sheet material which provides both the frame 104 and interior protector 105 is semi-rigid and is at least two-thousandths of an inch in thickness. As presently reduced to practice, the release-sheet material is about four-thousandths of an inch in thickness and, of course, on its exposed surface away from the adhesive provides a desired non-stick surface.

Although the medicator securing device as above shown and described is a rather simple device, it is believed to be quite novel used in and for medical applications. For this reason, several precautions are contemplated.

1. The self-stick adhesive must be non-toxic and selected from that group of adhesive materials that is suitable for use in a hospital. The self-stick adhesive when exposed and used with the above securing devices is within the frame and in normal and intended use is not in contact with the skin of the patient. This adhesive must be compatible with the film and frame material so as not to affect the properties of these components.

2. The self-supporting frame is usually made of a cardboard-like material, a release-sheet material or the like which is semi-rigid. Said frame may be one or more pieces and usually is scored or serrated to produce a fold line. Plastic sheet is also known and may be provided. Whatever the material, the frame must have one surface that is adapted for adherence to adhesive surface of the film and with the opposite surface of the frame adapted to have substantially a non-attractive capability so that the frame portions may be manipulated for separation.

3. The film is usually flexible and thin and, with an adhesive coating, is readily brought to and around the connectors so as to secure the assembled connection in the placed position. This film has sufficient strength to be pulled apart, exposing the connected portions of said connection so that it can and does form a second "skin" around this connection. The grasping and manipulating of the frame portions provide means for the pressed-together film portions to be pulled apart.

The configuration of the frame is a matter of choice and having sufficient body to prevent the medicator securing device from curling or otherwise distorting said securing device during storage prior to intended use. A fold of the frame or frames is contemplated, whether of less than a four-sided frame, such as in FIGS. 10 through 14, or a rectangular frame with or without a central portion. Any frame is adapted to have side extents grasped by the attendant and, with a pulling actuation, separate the frame portions and adhered flexible plastic films. The inner surfaces, prior to use, may be conventionally sterilized by the usual means.

It is desirable that this securing device be of inexpensive materials as it is intended for one-time use, after which it is discarded. The integrity of the connection must be and is retained. The flexible film is sufficiently strong to provide retention and protection of the connection during use in the patient. The attendant may use this device with little training as this securing procedure is similar to the taping of a connecton practiced prior to the invention of this device. The excluding of bacteria to and into the connection area is provided by the tightly engaged film. The attendant, since the film is transparent or substantially transparent, may view the connection and associated members to ascertain desired flow of medication and desired maintenance of insertion during use of the device. The frames may be grasped for easy pulling apart of the adhesive film areas.

Preferably, the frame is made substantially rectangular with a large window area or areas to provide exposure of flexible film for manipulative securing and for visual observation of administration. The design of the frame configuration is a matter of choice and shapes such as arcuate (D-shape) and the like are contemplated. It is desirable that a fold means be provided so that the film be secured tightly around the connection. The fold means is illustrated in the frame as in FIGS. 10 and 18 A. In the other extents, the frame provides a center web in which the fold capability is established. The composition and thickness of the frame need be semi-rigid to provide a means for retaining the flexible film on one surface while also providing means with or on the other surface for ready separation by grasping and manipulating said other surfaces of the frame that do not have the adhesively-coated film attached thereto. Release-sheet material is conventionally of a wax-coated paper, but sheet films are now available with non-stick surfaces. These films are finding their way into commercial use, particularly in connection with adhesively-attached female sanitary and panty pads.

The frame is showm above in several configurations which are intended to include beveled or other shaped inner and outer corners. Tab or other cutouts may be provided as in FIG. 17. In FIGS. 19 A and 19 B, the frame is shown made with release-sheet material, with the inner window-like area of the release sheet manipulated with a bending action to loosen a portion of said sheet from the adhesive surface of the film sufficient for removal.

All of the embodiments shown are contemplated to be made with high-speed automatic equipment, and it is known that such equipment lends itself to small tolerance deviations. It is contemplated that the flexible film will be furnished in rolls with the self-stick adhesive coating in place. Rotating or reciprocating dies are provided for cutting the film to the desired contour and these film members are then brought to the frame, which is also initially in roll form and is likewise die-cut. Pressing and assembling procedures are conventional. The release sheet is likewise die-cut and brought to the securing device. It is contemplated that small portions of the release sheet may overlay the frame so that portions are available and provide the desired access means for a fingernail and the like for removal of the release sheet. The release-sheet material may be used for both the frame and window covering as in FIGS. 19 A and 19 B or may extend partially intermediate the inner and outer extents of the frame to provide fingernail access means. Sterilization when and if contemplated may be performed initially. It is to be noted that the medicator securing device when in use provides protection of the connection by the surrounding films.

What is claimed is:

1. A medicator securing device comprising
a thin transparent flexible plastic film having an adhesive coating on one side;
a self-supporting frame secured to at least a portion of a periphery of said plastic film, said frame having a fold line for folding of said frame thereon to secure said film to itself and about a pair of connector components to secured the connector components together; and
a release sheet removably mounted over said adhesive coating on said plastic film.

2. A medicator securing device as set forth in claim 1 wherein said frame is of rectangular shape.

3. A medicator securing device as set forth in claim 1 wherein said frame is of U-shape.

4. A medicator securing device as set forth in claim 1 wherein said frame has a pair of rectangular portions disposed about said fold line for folding onto each other.

5. A medicator securing device as set forth in claim 1 wherein said plastic film is of a thickness of from 0.0005 to 0.004 inches.

6. A medicator securing device as set forth in claim 1 wherein said film has a pair of portions extending beyond said frame for adhesive securemenet together to secure said frame in a folded condition prior to use.

7. A medicator securing device as set forth in claim 6 wherein said film has a line of perforations between each extending portion and the remainder of said film to facilitate removal of said portions prior to folding of said frame about the connector components.

8. A medicator securing device comprising
a thin transparent flexible plastic film having an adhesive coating on one side;
a self-supporting frame secured to said plastic film, said frame having a pair of rectangular portions disposed for folding onto each other to secure said film to itself and about a pair of connector components to secure the connector components together; and
a release sheet removably mounted over said adhesive coating on said plastic film.

9. A medicator securing device as set forth in claim 8 wherein said film has a pair of portions extending beyond said frame for adhesive securement together to secure said frame in a folded condition prior to use.

10. A medicator securing device as set forth in claim 9 wherein said film has a line of perforations between each extending portion and the remainder of said film to facilitate removal of said portions prior to folding of said frame about the connector components.

11. In combination
a pair of connector components disposed in connected relation; and
a securing device for retaining said components in said connected relation, said device including a thin transparent plastic film folded about said connector components and having an adhesive coating thereon to secure said film to itself and to said components and a frame secured to said film to permit removal of said film from about said components upon manual separation of opposed portions of said frame from each other.

12. The combination as set forth in claim 11 wherein said components include a needle and a tubing connector member.

13. The combination as set forth in claim 11 wherein said frame is of rectangular shape.

14. The combination as set forth in claim 11 wherein said frame is of U-shape.

15. The combination as set forth in claim 11 wherein said frame has a pair of rectangular portions disposed about a common fold line.

* * * * *

UNITED STATES PATENT AND TRADEMARK OFFICE
CERTIFICATE OF CORRECTION

PATENT NO. : 4,801,296

DATED : January 31, 1989

INVENTOR(S) : Vincent L. Vaillancourt

It is certified that error appears in the above-identified patent and that said Letters Patent is hereby corrected as shown below:

```
Column 1, lines 36, 37 change "which this patent depicts" to
     -which depicts-
Column 1, line 39 change "As" to -An-
Column 1, line 67 change "preventing" to -presenting-
Column 4, line 16 change "retain" to -retainer-
Column 5, line 40 change "siad" to -said-
Column 6, line 10 change "connectoin" to  -- connection --.
Column 6, line 65 change ", and" to -, the-
Column 8, line 51 change "tubing, conductor" to -tubing
     conductor-
Column 11, line 12 change "showm" to -shown-
Column 11, line 52 change "secured" to -secure-
```

Signed and Sealed this

Twenty-fourth Day of October, 1989

Attest:

DONALD J. QUIGG

Attesting Officer

Commissioner of Patents and Trademarks